United States Patent
Kang et al.

(10) Patent No.: US 10,024,795 B2
(45) Date of Patent: Jul. 17, 2018

(54) METHOD FOR MONITORING VESICLES USING A MEMBRANE-PERMEABLE MARKER THAT IS CONVERTED INTO A MEMBRANE-NONPERMEABLE MARKER

(71) Applicant: Samsung Electronics Co., Ltd., Suwon-si, Gyeonggi-do (KR)

(72) Inventors: Hyun-ju Kang, Hwaseong-si (KR); Ye-ryoung Yong, Seoul (KR); Myo-yong Lee, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 893 days.

(21) Appl. No.: 13/785,945

(22) Filed: Mar. 5, 2013

(65) Prior Publication Data

US 2014/0099652 A1    Apr. 10, 2014

(30) Foreign Application Priority Data

Oct. 9, 2012 (KR) .................. 10-2012-0112094

(51) Int. Cl.
 *G01N 21/64* (2006.01)
 *G01N 33/58* (2006.01)
(52) U.S. Cl.
 CPC ......... *G01N 21/6486* (2013.01); *G01N 21/64* (2013.01); *G01N 21/6428* (2013.01); *G01N 33/582* (2013.01)
(58) Field of Classification Search
 None
 See application file for complete search history.

(56) References Cited

U.S. PATENT DOCUMENTS

| | | | | |
|---|---|---|---|---|
| 4,912,208 | A * | 3/1990 | Fiechtner | B82Y 5/00 536/53 |
| 5,854,082 | A * | 12/1998 | Kubotsu | G01N 33/5432 435/975 |
| 6,743,638 | B1 | 6/2004 | Tsilosani et al. | |
| 7,553,632 | B2 | 6/2009 | Niles et al. | |
| 7,951,550 | B2 | 5/2011 | Cali et al. | |
| 9,273,043 | B2 * | 3/2016 | Kurose | A61K 31/428 |
| 9,346,957 | B2 * | 5/2016 | Umezawa | C07F 7/081 |
| 9,394,293 | B2 * | 7/2016 | Yu | C07D 401/14 |
| 2010/0029791 | A1 | 2/2010 | Ichikawa et al. | |
| 2012/0075453 | A1 | 3/2012 | Kilpatrick et al. | |
| 2012/0164628 | A1 * | 6/2012 | Duffin | G01N 33/54366 435/5 |

(Continued)

OTHER PUBLICATIONS

Haney, MJ et al., "Blood-borne macrophage—neural cell interactions hitchhike on endosome networks for cell-based nanozyme brain delivery", Nanomedicine (2012) 7(6):815-833; epd: Jan. 11, 2012.*

(Continued)

*Primary Examiner* — Scott Long
*Assistant Examiner* — Gary E Hollinden
(74) *Attorney, Agent, or Firm* — Leydig, Voit & Mayer, Ltd.

(57) ABSTRACT

Provided is a method of monitoring a vesicle in a sample, including contacting a vesicle in a sample with a membrane permeable marker that is converted into a detectable marker in the vesicle, measuring a signal of the detectable marker, and monitoring the vesicle based on the measured signal.

8 Claims, 3 Drawing Sheets

(56) References Cited

U.S. PATENT DOCUMENTS

| | | | | |
|---|---|---|---|---|
| 2013/0178383 A1* | 7/2013 | Spetzler | ............ | G01N 33/5432 506/9 |
| 2013/0323756 A1* | 12/2013 | Tullis | ................ | G01N 33/5695 435/7.23 |
| 2016/0258962 A1* | 9/2016 | Battaglia | ............ | G01N 33/5005 |

OTHER PUBLICATIONS

Van der Pol E., "Classification, functions, and clinical relevance of extracellular vesicles", Pharmacol. Rev. (2012) 64(3): 676-705. PMID 22722893. doi:10.1124/pr.112.005983.*

György et al., "Membrane Vesicles, Current State-of-the-Art: Emerging Role of Extracellular Vesicles," *Cellular and Molecular Life Sciences*, 68: 2667-2688 (2011).

Tauro et al., "Comparison of Ultracentrifugation, Density Gradient Separation, and Immunoaffinity Capture Methods for Isolating Human Colon Cancer Cell Line LIM1863-Derived Exosomes," *Methods*, 56: 293-304 (2012).

Yuana et al., "Chapter 2: Pre-Analytical and Analytical Issues in the Analysis of Blood Microparticles," *Thrombosis Haemostasis*, 105(3): 396-408 (2010).

Astion, Michael L. et al. "Classifying Laboratory Incident Reports to Identify Problems That Jeopardize Patient Safety," *American Society for Clinical Pathology*, 120, pp. 18-26 (2003).

Carraro, Paolo et al. "Error in a Stat Laboratory: Types and Frequencies 10 Years Later," *Clinical Chemistry*, 55:7, pp. 1338-1342 (2007).

Korean Office Action in Application No. 10-2012-0112094 dated Mar. 16, 2018.

Mitchell et al., "Can urinary exosomes act as treatment response markers in prostate cancer?" *Journal of Translational Medicine*, 7:4, pp. 1-13 (2009).

Bernimoulin et al., "Differential stimulation of monocytic cells results n distinct populations of microparticles", *J Thromb Haemost*; 7(6), pp. 1019-1028 (2009).

Di Virgilio et al., "Inhibition of Fura-2 sequestration and secretion with organic anion transport blockers", *PubMed , Cell Calcium*, 11(2-3) (1990).

* cited by examiner

METHOD FOR MONITORING VESICLES USING A MEMBRANE-PERMEABLE MARKER THAT IS CONVERTED INTO A MEMBRANE-NONPERMEABLE MARKER

CROSS-REFERENCE TO RELATED APPLICATIONS

This application claims the benefit of Korean Patent Application No. 10-2012-0112094, filed on Oct. 9, 2012 in the Korean Intellectual Property Office, the disclosures of which are incorporated herein in their entirety by reference.

BACKGROUND

1. Field

The present disclosure relates to compositions and kits for monitoring vesicles, and methods for monitoring vesicles using the same.

2. Description of the Related Art

In vivo microvesicles are small membranous vesicles that exist in or are secreted from various cell types. Microvesicles secreted from cells include: (i) exosomes, which are membranous vesicles that originate from phagocytic cells and have a diameter of 30 to 100 nm; (ii) ectosomes (also called shedding microvesicles (SMVs)), which are membranous vesicles that are released from the plasma membrane and have a diameter of 50 to 1000 nm; and (iii) apoptotic blebs, which are vesicles that are secreted from dying cells and have a diameter of 50 to 5000 nm.

Electron microscopy has confirmed that exosomes do not separate directly from the plasma membrane, but originate in particular intracellular regions called multivesicular bodies (MVBs). Multivesicular bodies fuse with the plasma membrane of cells and are then released from the cells as exosomes. Exosomes are released from a plurality of cell types under normal and/or pathologic states. Although the molecular mechanisms of exosomes are unknown, it is known that, in addition to red blood cells, various kinds of immune cells, such as B-lymphocyte, T-lymphocyte, dendritic cells, blood platelets, and macrophage, and tumor cells, produce and secrete exosomes. In vivo microvesicles, such as exosomes, may contain microRNA (miRNA), which may be used as a marker in molecular diagnosis, such as early diagnosis of cancer.

Experimental bias may be introduced during the collection, handling, storage, or analysis of microvesicle samples. For example, in centrifugation, graduations may become mixed, or microvesicle sample loss or contamination may occur when removing supernatant. In immune capture, yield rates may vary. In filtration, the quantity and quality of filtrate may vary based on the viscosity of microvesicle samples.

Therefore, there is a need for improved compositions and methods for monitoring vesicles, processes using vesicles, and the quality of vesicle samples.

SUMMARY

Provided is a composition for monitoring a vesicle in a sample, the composition including a membrane permeable marker that is converted into a detectable marker in the vesicle.

Also provided is a method of monitoring a vesicle in a sample, the method comprising contacting a vesicle in a sample with a membrane permeable marker that is converted into a detectable marker in the vesicle; measuring a signal of the detectable marker; and monitoring the vesicle based on the measured signal. Related methods, compositions, and kits also are provided.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
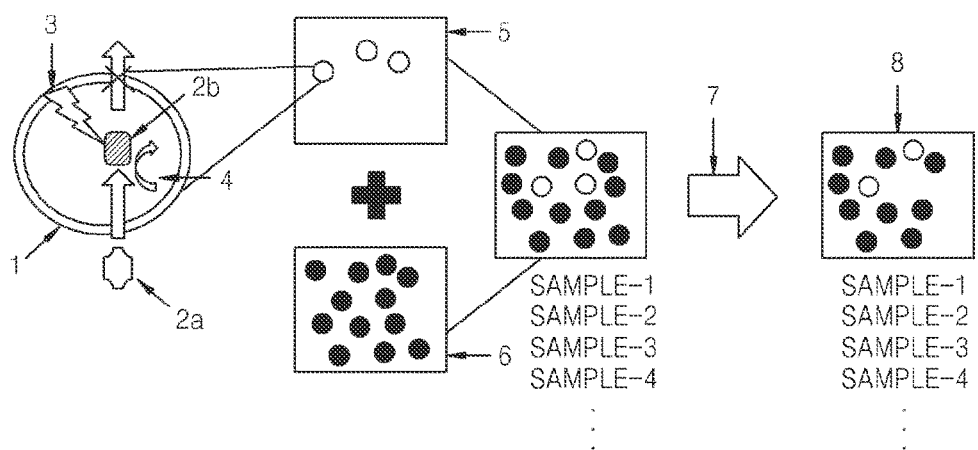
FIG. 1 is a schematic diagram that illustrates a method of monitoring vesicles in samples using a membrane permeable marker that is converted into a detectable marker in the vesicles, wherein (1) is a vesicle compartmentalized with a lipid layer, (2a) is a membrane permeable marker, (2b) is a membrane permeable marker converted into a detectable marker once inside the vesicle, (3) is a signal originating from the detectable marker, (4) is a reaction that converts the membrane permeable marker into the detectable marker, (5) are vesicles that are fluorescently marked as an internal control group, (6) is a sample including vesicles of an unknown quantity, (7) is a pre-analysis/analysis process, and (8) are vesicles obtained after the process.

Provided is a composition for monitoring a vesicle in a sample, including a membrane permeable marker that is converted into a detectable marker in the vesicle.

"Vesicle" refers to a membranous structure that is surrounded by a lipid bilayer. For example, the vesicle may be a liposome or a microvesicle. "Microvesicle" refers to a small vesicle with a membranous structure that originates from a cell. The term microvesicle may be interchangeably used herein with the terms circulating microvesicle or microparticle. Microvesicles may exist in cells or may be secreted from cells. Microvesicles secreted from cells may include exosomes, ectosomes (shedding microvesicles (SMVs)), apoptotic blebs, or any combination thereof. Exosomes are membranous vesicles of about 30 to about 100 nm diameter that originate from phagocytes. Ectosomes (SMVs) are large membranous vesicles of about 50 to about 1000 nm diameter that are directly released from plasma membranes. Apoptotic blebs are vesicles of about 50 to about 5000 nm diameter that are leaked from dying cells. In vivo microvesicles may contain microRNAs (miRNAs) or messenger RNAs (mRNAs). Surface proteins of microvesicles may be disease-specific markers.

The membrane permeable marker that is converted into a detectable marker in the vesicle may be converted into a fluorescent material within the vesicle. "Fluorescent material" refers to a material that emits light under a change of physical conditions or chemical treatments. The fluorescent material may be a non-fluorescent material outside of a microvesicle, but may be converted into a fluorescent material once inside a microvesicle. The conversion may be performed by enzymes within the microvesicle. For example, the enzyme may be esterase. Also, the marker may be a hydrophobic material, but may be converted into a hydrophilic material inside vesicles. The hydrophobic marker material will be able to penetrate vesicles so as to gain entry to the vesicles, but the marker converted into a hydrophilic material inside the vesicles will not be able to penetrate vesicles to escape unless the vesicle is ruptured.

Any suitable method may be used for measuring the signal. Various methods are known in the art. For example, if the marker is a fluorescent material such as a fluorescent protein, the fluorescence intensity generated when the fluorescent protein is exposed to ultraviolet light may be measured using a fluorophotometer.

The marker may be, for example, an ester (e.g., acetoxymethyl ester) of a fluorescent group, wherein the esterified compound does not fluoresce under activating conditions (e.g., ultraviolet light) until the ester is cleaved by an esterase. Specific examples of such compounds include, for instance, Calcein-AM (Calcein-acetoxymethyl ester), Fura-2-AM (Fura-2-acetoxymethyl ester), Indo-1-AM (Indo-1-acetoxymethyl ester), Indo-5F-AM (Indo-5F-acetoxymethyl ester), Quin-2-AM (Quin-2-acetoxymethyl ester), 5-CFDA-AM (5-Carboxyfluorescein Diacetate-acetoxymethyl ester), BAPTA-AM (bis(2-aminophenoxy)ethane tetraacetic acid-acetoxymethyl ester), 5,5'-difluoro BAPTA-AM, 5,5'-dimethyl BAPTA-AM, 5,5'-dinitro BAPTA-AM, BCECF-AM (2',7'-bis-(2-carboxyethyl)-5-(and-6)-carboxyfluorescein acetoxymethyl ester), dihydrocalcein-AM (dihydrocalcein-acetoxymethyl ester), EGTA-AM (EGTA-acetoxymethyl ester), Fluo-3-AM (Fluo-3-acetoxymethyl ester), Fluo-8-AM (Fluo-8-acetoxymethyl ester), Rhod-2-AM (Rhod-2-acetoxymethyl ester), Rhod-4-AM (Rhod-2-acetoxymethyl ester), Rhod-5F-AM (Rhod-5F-acetoxymethyl ester), Rhod-5N-AM (Rhod-5N-acetoxymethyl ester), X-Rhod-1-AM (X-Rhod-1-acetoxymethyl ester), Cal-520™, or any combinations thereof.

The sample may be a body fluid or cell culture. The body fluid may be, for example, urine, mucus, saliva, tears, blood plasma, blood serum, sputum, spinal fluid, hydrothorax fluid (fluid from the pleural cavity), nipple aspirate, lymph, tracheolar fluid, intestinal juice, genitourinary tract fluid, breast milk, semen, ascites fluid (peritoneal fluid), cystic tumor fluid, amniotic fluid, or any combinations thereof. The sample may be intact cells, dead cells, or cell debris. The sample may be pretreated with centrifugation, dialysis, or any combinations thereof.

The monitoring of the status of a vesicle in the sample may be performed by measuring a signal of the marker that is converted into the detectable marker (i.e., the signal of the detectable marker once formed). For example, the monitoring may be an analysis of the quantitative or qualitative status of vesicles in the samples. The vesicles may be used as an internal control group. For example, a process may be monitored by comparing the fluorescence intensities of the detectable marker before and after the process. Also, the degradation of vesicles in a sample may be identified by comparing fluorescence intensities at an initial stage and at a later stage. In addition, vesicles marked with a fluorescent material may be injected into cells or a body and then traced.

The composition may further include an organic anion transport inhibitor. "Organic anion transport inhibitor" refers to a material that inhibits an organic anion transport system. For example, the organic anion transport inhibitor may be sulfinpyrazone, probenecid, betamipron, cilastatin, 8-(noradamantan-3-yl)-1,3-dipropylxanthine, or any combination thereof. The monitoring efficiency of vesicles may be enhanced by using a organic anion transport inhibitor.

Provided is a kit for monitoring vesicles in a sample including a membrane permeable marker that is converted into a detectable marker in the vesicles. The kit may include any of the previously described components, including a detectable marker and an organic anion transport inhibitor.

Also provided is method of monitoring a vesicle in a sample including: contacting a vesicle in a sample with a membrane permeable marker that is converted into a detectable marker in the vesicle; measuring a signal of a marker that is converted into the detectable marker; and monitoring the status of the vesicle from the measured signal.

The sample may be contacted with the membrane permeable marker by any suitable technique. For instance, the sample can combined with the membrane permeable marker, whereupon the membrane permeable marker will contact the vesicles contained in the sample and penetrate the vesicles. Once inside the vesicles, the membrane permeable marker is converted into a detectable marker, from which a signal can be measured or detected and used to monitor the status of the vesicle.

In another embodiment, the method can comprise contacting isolated or purified vesicles with a membrane permeable marker, whereupon the membrane permeable marker will contact the vesicles contained in the sample and penetrate the vesicles to be converted to detectable markers, and the vesicles containing the detectable markers can then be combined with a sample (e.g., a biological sample) comprising vesicles. The vesicles comprising the marker may, then, serve as a control by which processing of the sample can be monitored. For instance, the vesicles comprising the marker can be added to the biological sample in a known quantity or concentration, and the efficiency or effectiveness of processing steps (isolation, purification, etc.) can be monitored based on the recovered quantity or quality (lysed or whole) control vesicles. The contacting may be performed in vitro. The contacting may be performed at room temperature. The contacting may be performed while mixing reactants.

The method may include measuring a signal of the detectable marker by any suitable technique, as previously described.

The method may include analyzing the status of the vesicle from the measured signal. The status of the vesicle may be a quantitative or qualitative status of the vesicle.

The monitoring the vesicle in the sample may be performed by measuring a signal of the detectable marker (e.g., after conversion from the membrane permeable marker). For example, the monitoring may be an analysis of a quantitative or qualitative status of vesicles in the samples. In the case of monitoring vesicles by using the vesicles as an internal control group, the process may be monitored by comparing fluorescence intensities before and after the process. Also, qualities, such as degradation of vesicles in samples, may be identified by comparing fluorescence intensities in an initial stage and an actual use. In addition, in the case of injecting vesicles marked with a fluorescent material into cells or a body, locations of the vesicles in the cells or body may be traced.

The method may further include incubating the sample, or isolated or purified microvesicles, with an organic anion transport inhibitor, followed by the measuring of the signal of the marker that is converted into the detectable marker. The organic anion transport inhibitor may be any of those previously described. The incubating may be performed at room temperature. The incubating may be performed while mixing reactants. The incubating of the organic anion transport inhibitor and the sample may be performed before, after, or at the same time of the contacting of the membrane permeable marker that is converted into the detectable marker in the vesicle with the sample. The monitoring efficiency of vesicles may be enhanced by incubating the sample with the organic anion transport inhibitor.

The method may be used for any purpose, such as to monitor the status of vesicles, to perform quality control, and/or to trace the location of vesicles.

EXAMPLES

Example 1. Quantification and Stability of Microvesicles as an Internal Control Group It was identified whether microvesicles marked with calcein-AM might be stably used as a quantitative control.

Figure 2A:
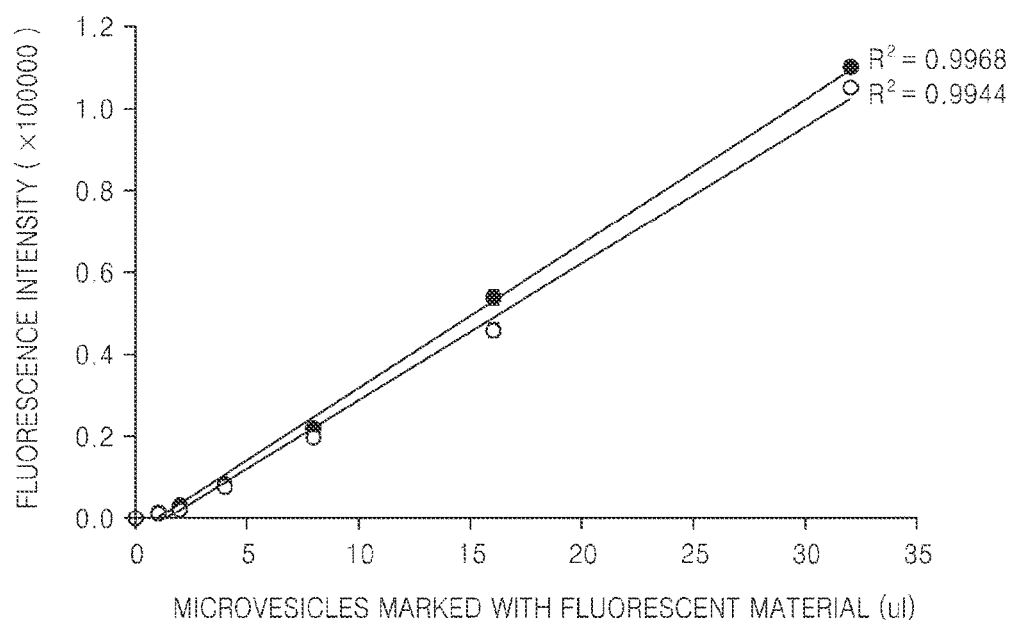
FIGS. 2A and 2B are graphs of fluorescence plotted against the quantity of plasma (microliters) used for preparing labeled microvesicles marked with fluorescent material, which illustrate quantification and stability, respectively, of microvesicles that are marked with purified fluorescent materials. The quantity of plasma indirectly reflects the quantity of microvesicles used.

Microvesicles and calcein-AM were mixed and incubated to produce microvesicles marked with calcein-AM. About 0 to about 100 μl of blood plasma was added to the microvesicles marked with calcein-AM and then washed. Then, the fluorescent intensity was measured using a fluorophotometer (Beckman, DTX800). As a result, as shown in FIG. 2A, it was identified that quantification exists when microvesicles marked with calcein-AM were mixed with blood plasma (●: blood plasma 0 μl, ○: blood plasma 20 μl).

Figure 2B:
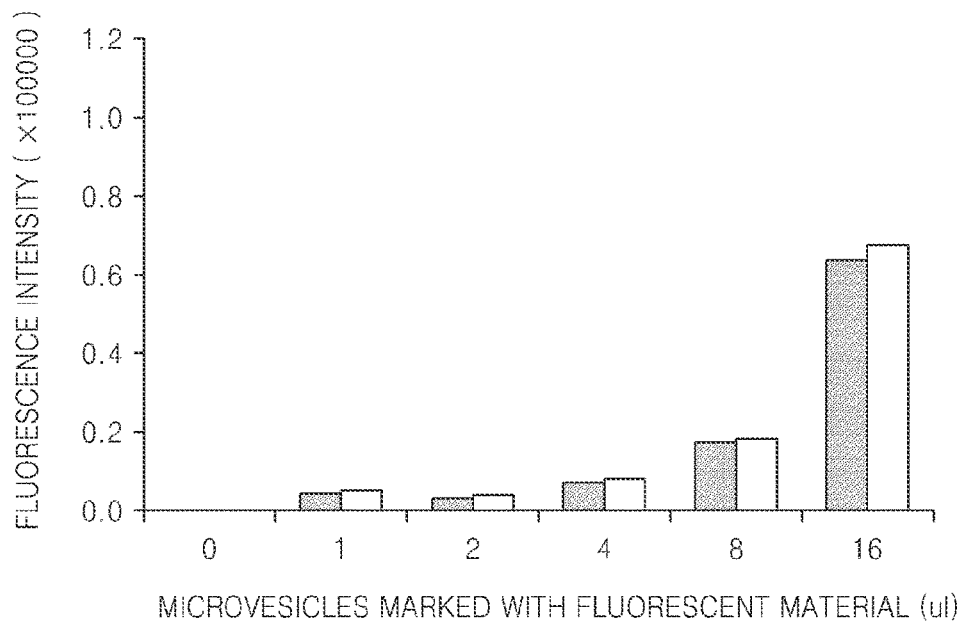

Microvesicles marked with calcein-AM were left for 20 hours at room temperature in the dark and then fluorescence intensity was measured. As a result, as shown in FIG. 2B, there was no change in fluorescence intensity after having stored the microvesicles marked with calcein-AM (■: 5 minutes, □: 20 hours). Therefore, it was identified that microvesicles marked with calcein-AM were stable and hence could be used as a control.

Example 2. Process Monitoring

The following example illustrates the use of microvesicles marked with calcein-AM that were prepared in Example 1 to monitory or analyze capture recovery of microvesicles in samples.

The recovery of microvesicles before and after capturing microvesicles with anti-CD9 antibody was identified by measuring the fluorescence intensity of the microvesicles marked with calcein-AM that were prepared in Example 1 and the fluorescence intensity of microvesicles marked with calcein-AM that were recovered after capturing microvesicles with anti-CD9 antibody.

Figure 3:
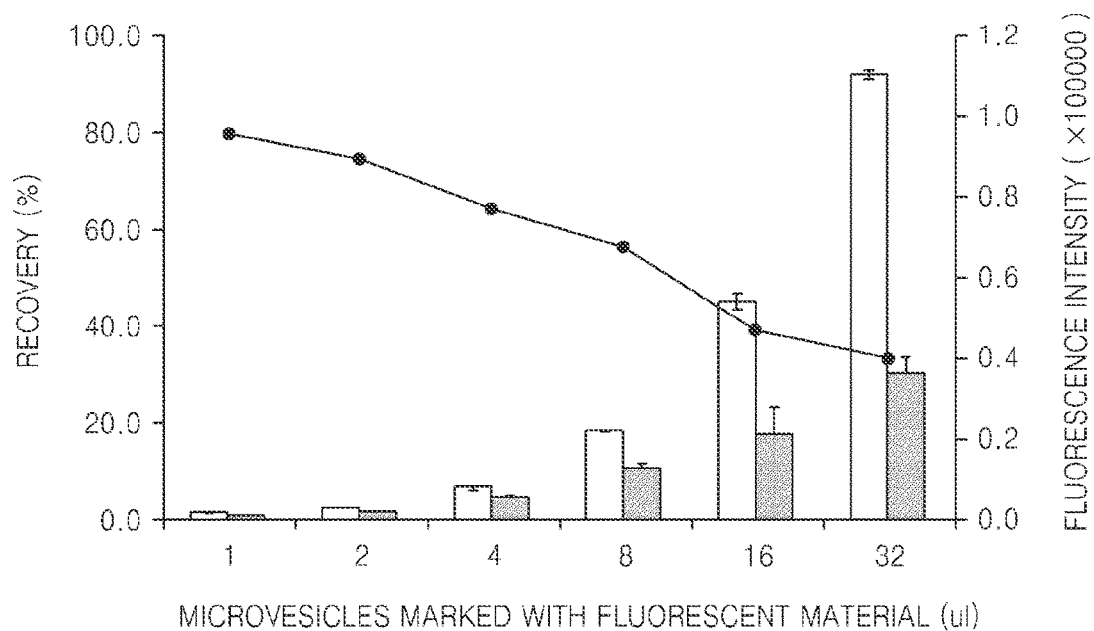
FIG. 3 is a graph of percent-recovery plotted against the quantity of plasma (microliters) used for preparing labeled microvesicles, which illustrates a result of monitoring a process using microvesicles that are marked with a fluorescent material. The quantity of plasma indirectly reflects the quantity of microvesicles used.

Moreover, as shown in FIG. 3, an antibody capture recovery was also calculated via the intensity comparison before and after capturing with an anti-CD9 antibody. As shown in FIG. 3, the recovery (%) changed from 32.9% to 79.6% according to the input microvesicle amount (1 μl to 32 μl) (□: initial, ■: after capturing with anti-CD9 antibody, ●: recovery)

Example 3. Quality Control of Samples Containing Microvesicles

To monitor the change of microvesicles in samples due to storage conditions, the change in quantity and surface proteins of microvesicles was identified by repeating freezing and thawing.

Figure 4A:
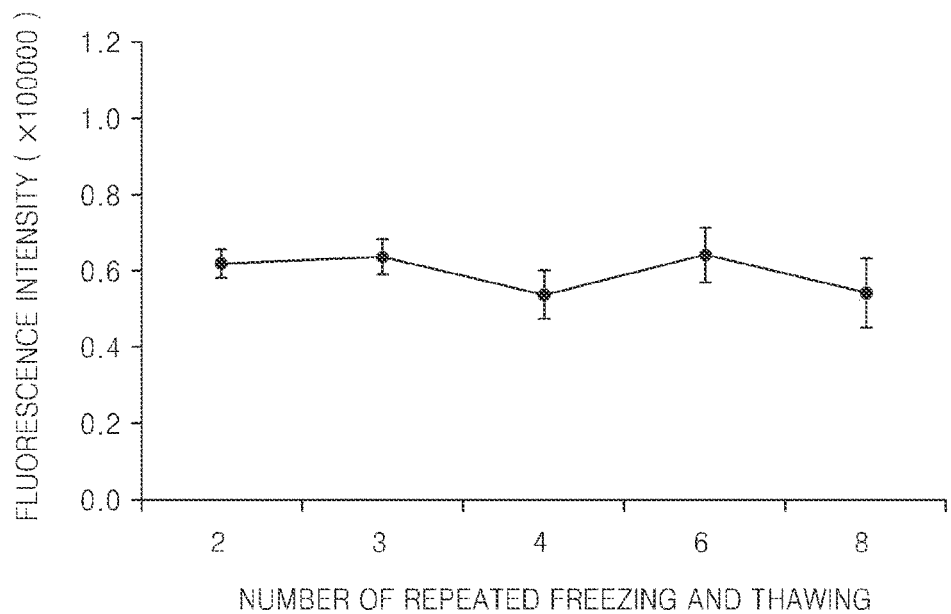
FIGS. 4A and 4B are graphs of fluorescence plotted against the number of freeze/thaw cycles, which illustrate the use of microvesicles that are marked with a fluorescent material to monitor the quality of the microvesicles.

Microvesicles marked with calcein-AM and blood plasma were mixed and incubated, and then freezing and thawing were repeated. Afterwards, the reactant was filtered, and the fluorescence intensity was measured. As shown in FIG. 4A, the quantity of microvesicles was not significantly changed even after the repetition of 8 freezing and thawing cycles.

Figure 4B:
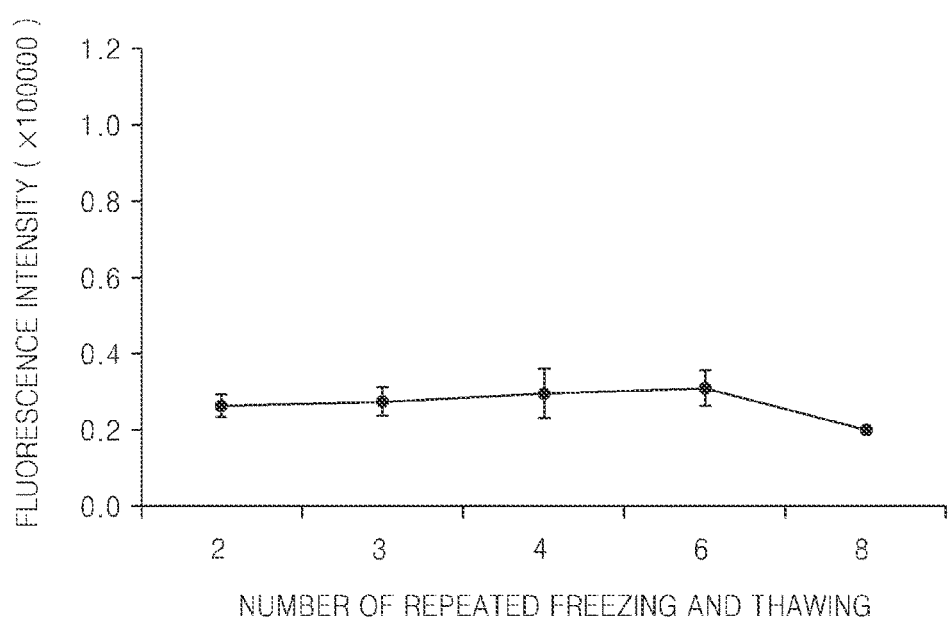

Microvesicles marked with calcein-AM and blood plasma were mixed and incubated, and then were immunoprecipitated with anti-CD9 antibody. Afterwards, freezing and thawing were repeated and then the fluorescence intensity was measured. As shown in FIG. 4B, the fluorescence intensity decreased by about 14.3% to about 20.8% ($P<0.05$) when freezing and thawing were repeated 6 to 8 times. Therefore, it was identified that surface proteins of microvesicles were significantly changed over the course of 6 to 8 freezing and thawing cycles.

It should be understood that the exemplary embodiments described therein should be considered in a descriptive sense only and not for purposes of limitation. Descriptions of features or aspects within each embodiment should typically be considered as available for other similar features or aspects in other embodiments.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of monitoring a process using a sample, the method comprising:
   mixing the sample with an exosome marked with a membrane permeable marker and comprising an esterase;
   measuring a signal of the detectable fluorescent marker; and
   monitoring the process using the sample based on the measured signal,
   wherein the membrane permeable marker is a compound comprising an ester of a fluorescent group and is converted into a detectable fluorescent marker by the esterase in the exosome, and the compound does not fluoresce until the ester is cleaved by the esterase.

2. The method of claim 1, wherein the membrane permeable marker is Calcein-AM (Calcein-acetoxymethyl ester), Fura-2-AM (Fura-2-acetoxymethyl ester), Indo-1-AM (Indo-1-acetoxymethyl ester), Indo-5F-AM (Indo-5F-acetoxymethyl ester), Quin-2-AM (Quin-2-acetoxymethyl ester), 5-CFDA-AM (5-Carboxyfluorescein Diacetate-acetoxymethyl ester), BAPTA-AM (bis(2-aminophenoxy)ethane tetraacetic acid-acetoxymethyl ester), 5,5'-difluoro BAPTA-AM, 5,5'-dimethyl BAPTA-AM, 5,5'-dinitro BAPTA-AM, BCECF-AM (2',7'-bis-(2-carboxyethyl)-5-(and-6)-carboxyfluorescein acetoxymethyl ester), dihydrocalcein-AM (dihydrocalcein-acetoxymethyl ester), EGTA-AM (EGTA-acetoxymethyl ester), Fluo-3-AM (Fluo-3-acetoxymethyl ester), Fluo-8-AM (Fluo-8-acetoxymethyl ester), Rhod-2-AM (Rhod-2-acetoxymethyl ester), Rhod-4-AM (Rhod-2-acetoxymethyl ester), Rhod-5F-AM (Rhod-5F-acetoxymethyl ester), Rhod-5N-AM (Rhod-5N-acetoxymethyl ester), X-Rhod-1-AM (X-Rhod-1-acetoxymethyl ester), or any combinations thereof.

3. The method of claim 1, wherein the exosome further comprises an organic anion transport inhibitor.

4. The method of claim 3, wherein the organic anion transport inhibitor is sulfinpyrazone, probenecid, betamipron, cilastatin, 8-(noradamantan-3-yl)-1,3-dipropylxanthine, or any combinations thereof.

5. The method of claim 1, wherein the sample is body fluid or cell culture.

6. The method of claim 1, wherein the sample is urine, mucus, saliva, tears, blood plasma, blood serum, sputum, spinal fluid, hydrothorax, nipple aspirate, lymph, tracheolar fluid, intestinal juice, genitourinary tract fluid, breast milk, semen, ascites, cystic tumor fluid, amniotic fluid, or any combination thereof.

7. A method of monitoring quality of a sample, the method comprising:
   mixing the sample with an exosome marked with a membrane permeable marker and comprising an esterase;
   measuring signals of the detectable fluorescent marker; and
   monitoring the quality of the sample based on a change in the measured signals,
   wherein the membrane permeable marker is a compound comprising an ester of a fluorescent group and is converted into a detectable fluorescent marker by the esterase in the exosome, and the compound does not fluoresce until the ester is cleaved by the esterase.

8. A method of monitoring efficiency of isolating exosomes from a sample, the method comprising:
   mixing the sample with an exosome marked with a membrane permeable marker and comprising an esterase;
   measuring a signal of the detectable fluorescent marker before and after isolation of exosomes from the sample; and
   monitoring the efficiency of isolating exosomes from the sample based on the measured signal,
   wherein the membrane permeable marker is a compound comprising an ester of a fluorescent group and is converted into a detectable fluorescent marker by the esterase in the exosome, and the compound does not fluoresce until the ester is cleaved by the esterase.

* * * * *